United States Patent
Kazama et al.

(10) Patent No.: US 6,694,815 B2
(45) Date of Patent: Feb. 24, 2004

(54) LIQUEFACTION PHENOMENON PREDICTION SYSTEM

(75) Inventors: Motoki Kazama, Sendai (JP); Noriaki Sentou, Sendai (JP); Akira Yamaguchi, Tagajyou (JP)

(73) Assignee: Tohoku Techno Arch Co., Ltd. (JP)

( * ) Notice: Subject to any disclaimer, the term of this patent is extended or adjusted under 35 U.S.C. 154(b) by 0 days.

(21) Appl. No.: 10/387,636

(22) Filed: Mar. 13, 2003

(65) Prior Publication Data

US 2003/0177834 A1 Sep. 25, 2003

(30) Foreign Application Priority Data

Mar. 20, 2002 (JP) .......................... 2002-079474

(51) Int. Cl.$^7$ ............................. G01N 29/12; G01S 3/80
(52) U.S. Cl. ............................. 73/584; 73/784; 73/789; 73/823
(58) Field of Search ............................. 73/584, 37, 38, 73/784, 789, 798, 803, 822, 823

(56) References Cited

U.S. PATENT DOCUMENTS

| | | | |
|---|---|---|---|
| 5,127,267 A | * 7/1992 | Huebler et al. | 73/584 |
| 5,243,855 A | * 9/1993 | Stieger et al. | 73/153 |
| 5,412,989 A | * 5/1995 | Eberle et al. | 73/592 |
| 5,691,481 A | * 11/1997 | Nishida | 73/790 |
| 5,850,043 A | * 12/1998 | Robinett | 73/786 |
| 5,911,164 A | * 6/1999 | McRae | 73/815 |
| 5,931,237 A | * 8/1999 | Henke et al. | 73/84 |
| 6,003,376 A | * 12/1999 | Burns et al. | 73/584 |

OTHER PUBLICATIONS

"1223 Flow Deformation Mechanism Due to Seepage Failure After Earthquake", Kazam et al., The 36th Geotechnical Engineering Symposium (Tokushima), Jun., 2001, pp. 2415–2416.

"1224 Prediction Method of Flow Deformation Due to Seepage Failure After Earthquake" Sentou et al., The 36th Geotechnical Engineering Symposium (Tokushima), Jun., 2001, pp. 2417–2418.

"Liquefaction Prediction/Determination" Port Harbour Research Institute, *Handbook on Liquefaction Remediation of Reclaimed Land*, 1997, pp. 107–117.

"Recent Advances and Future Trends in Liquefaction/Damage Evaluation" Port Harbour Institute, *Handbook on Liquefaction Remediation of Reclaimed Land*, 1997, pp. 220–229.

* cited by examiner

*Primary Examiner*—Hezron Williams
*Assistant Examiner*—Jacques Saint-Surin
(74) *Attorney, Agent, or Firm*—Hayes Soloway P.C.

(57) ABSTRACT

To predict residual settlement quantity and residual horizontal deformation quantity of ground where a liquefaction phenomenon has occurred due to earthquake. Soils in situ (stratum B to stratum D) are sampled from ground, and are made to be element test object stratums. A stratum whose characteristic is well-known, or the like may be substituted for a numerical model (stratum A). Next, setting of input conditions is performed, and vertical stress, horizontal stress and initial shear stress, which are equivalent to applied load that the ground at a depth of the point suffers, are worked on to each stratum. This recreates a stress status of soil before earthquake occurs. Then, shear displacement and the movement quantity of interstitial water by earthquake are given to the test piece, and the quantity of shear stress and pore water pressure, which have occurred, is obtained. In the element test execution stratum, displacement computed for stratum element and the movement quantity of interstitial water are actually given to each element to measure restoring force and the pore water pressure. By sequentially repeating the steps, it is possible to simulate the behavior of the liquefaction phenomenon.

4 Claims, 9 Drawing Sheets

[Fig.01]
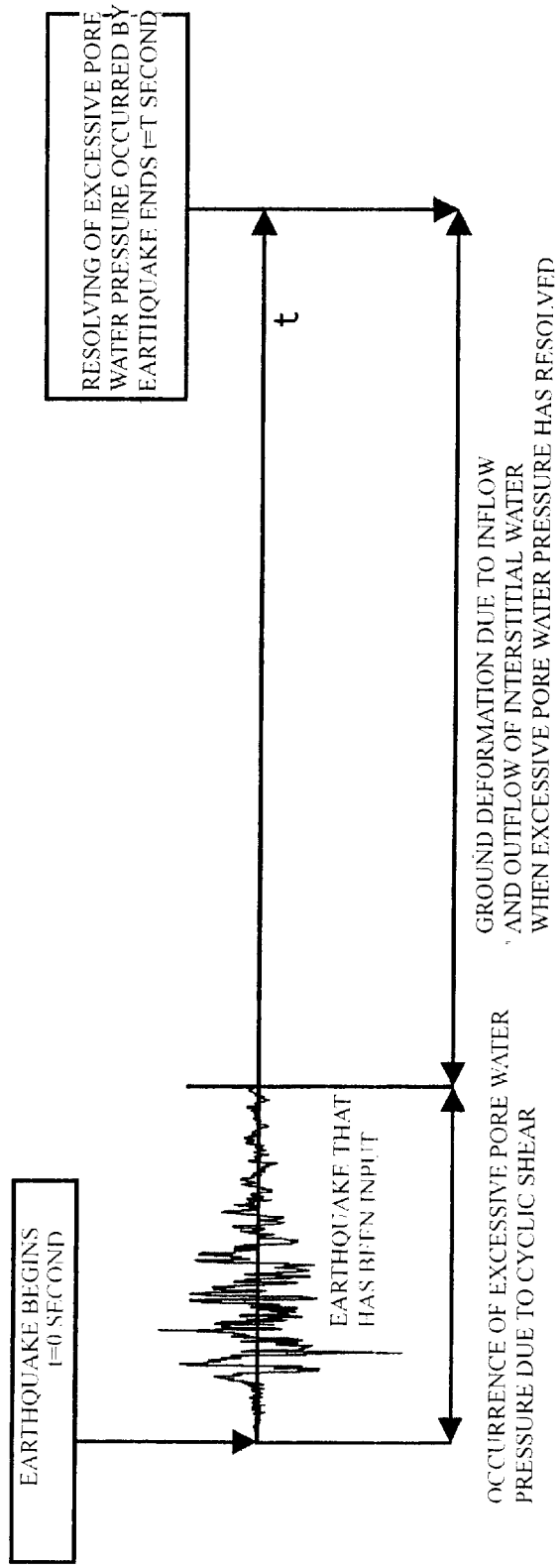

[Fig.02]
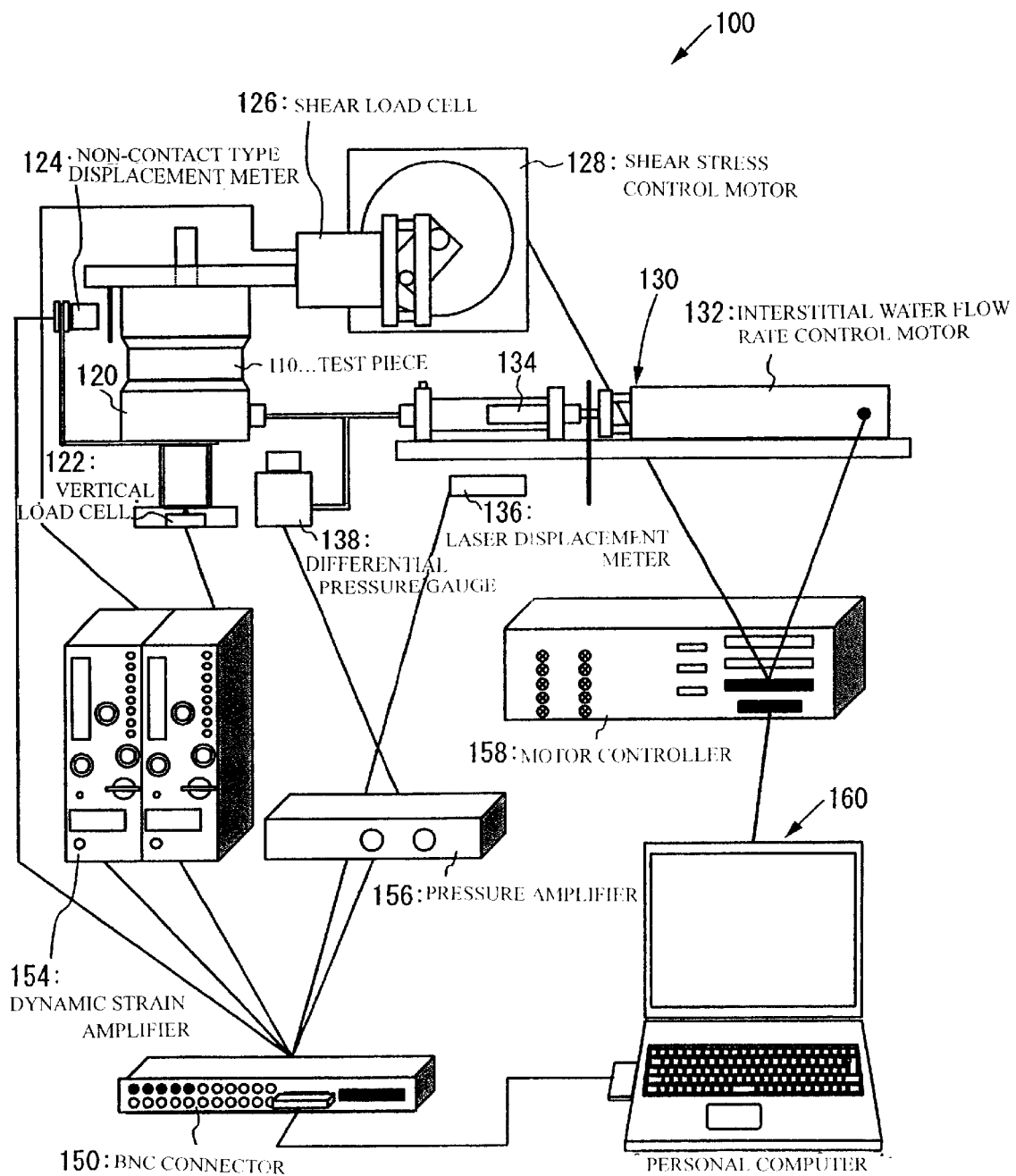

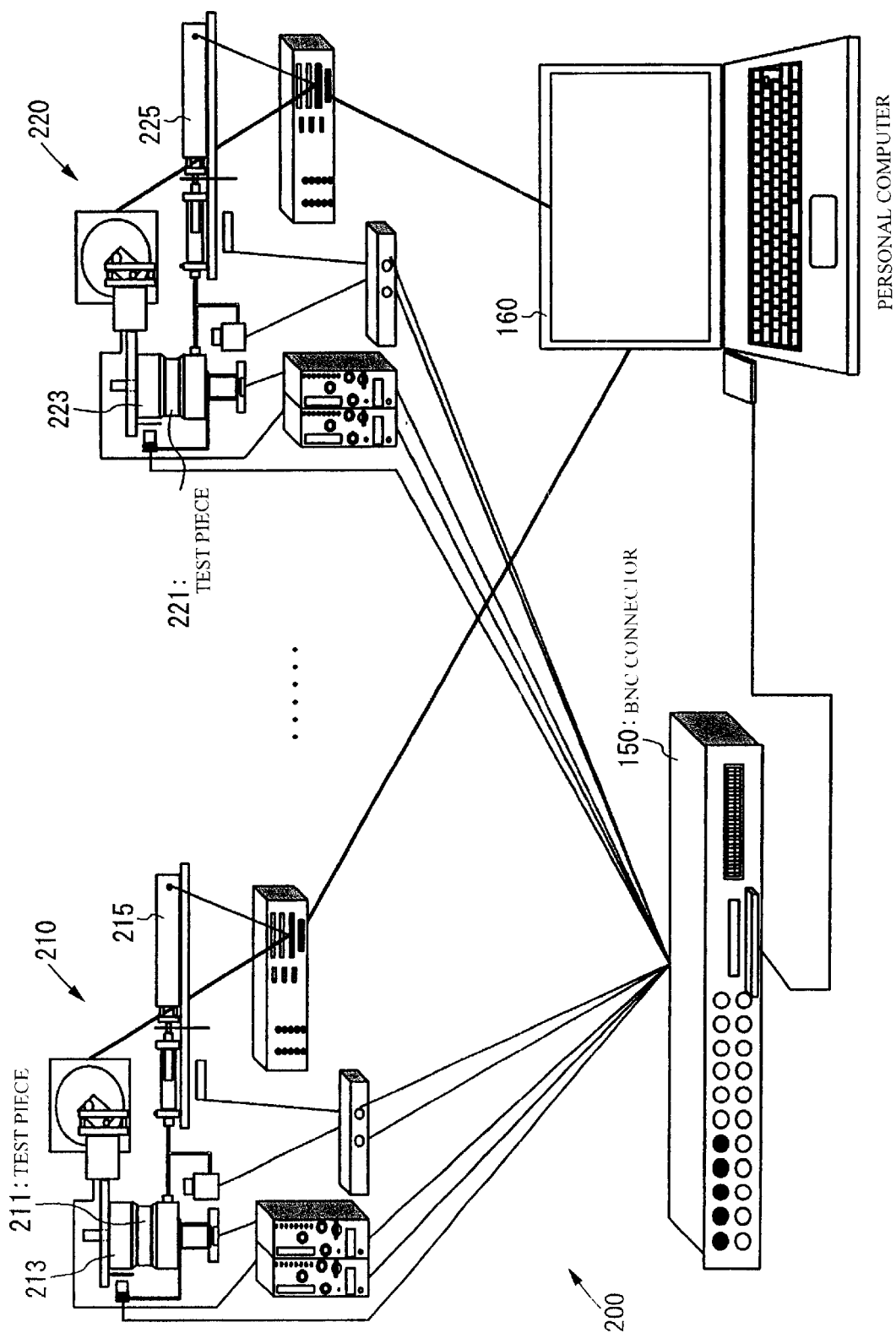
[Fig.03]

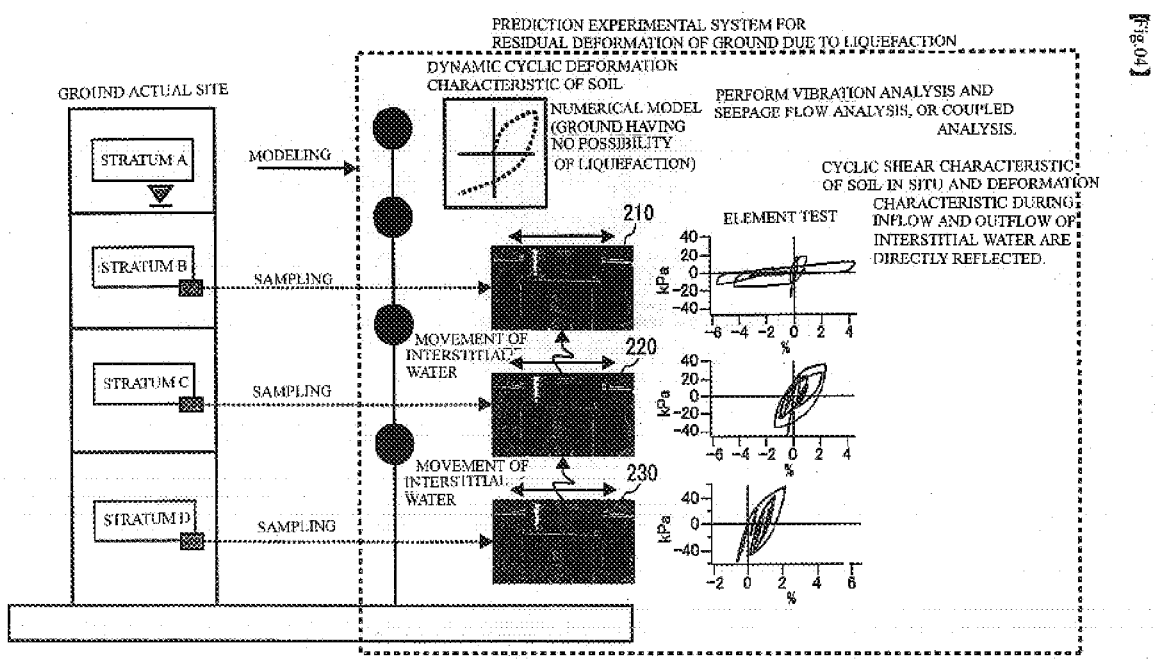

[Fig.05]
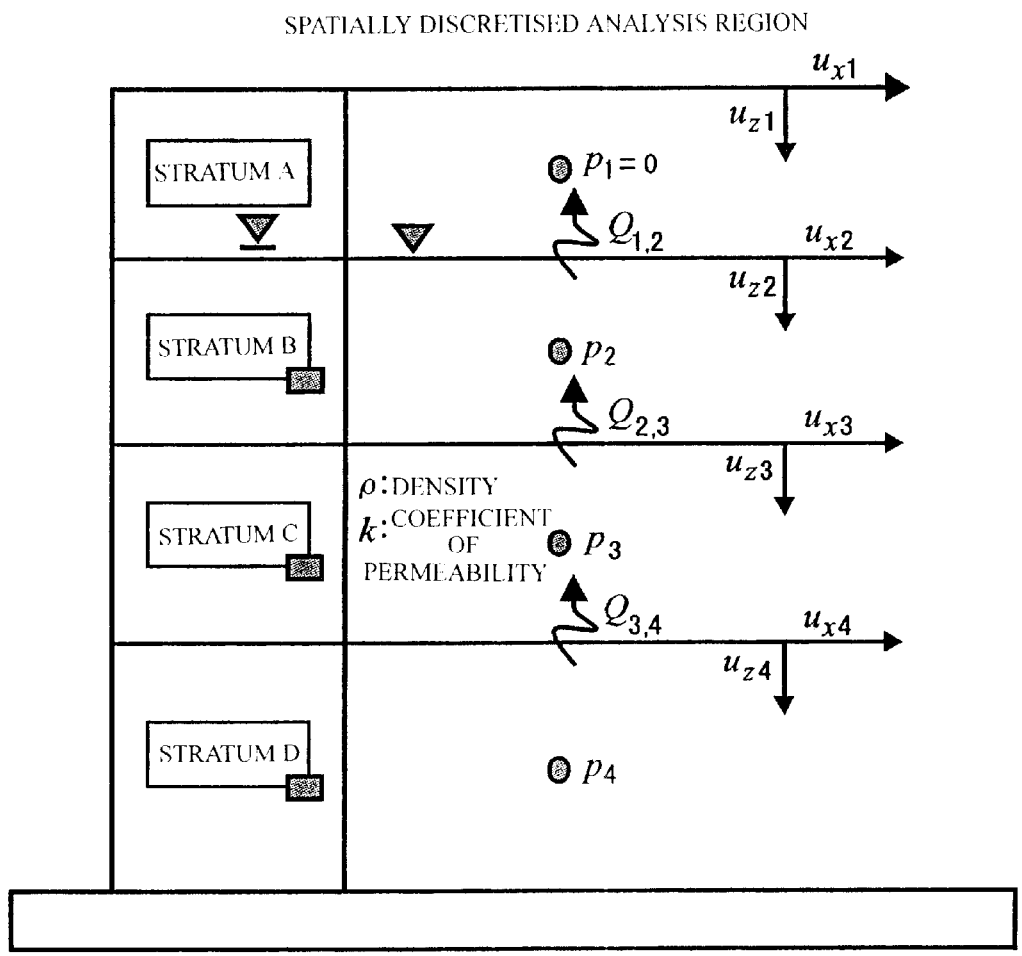

[Fig.06]
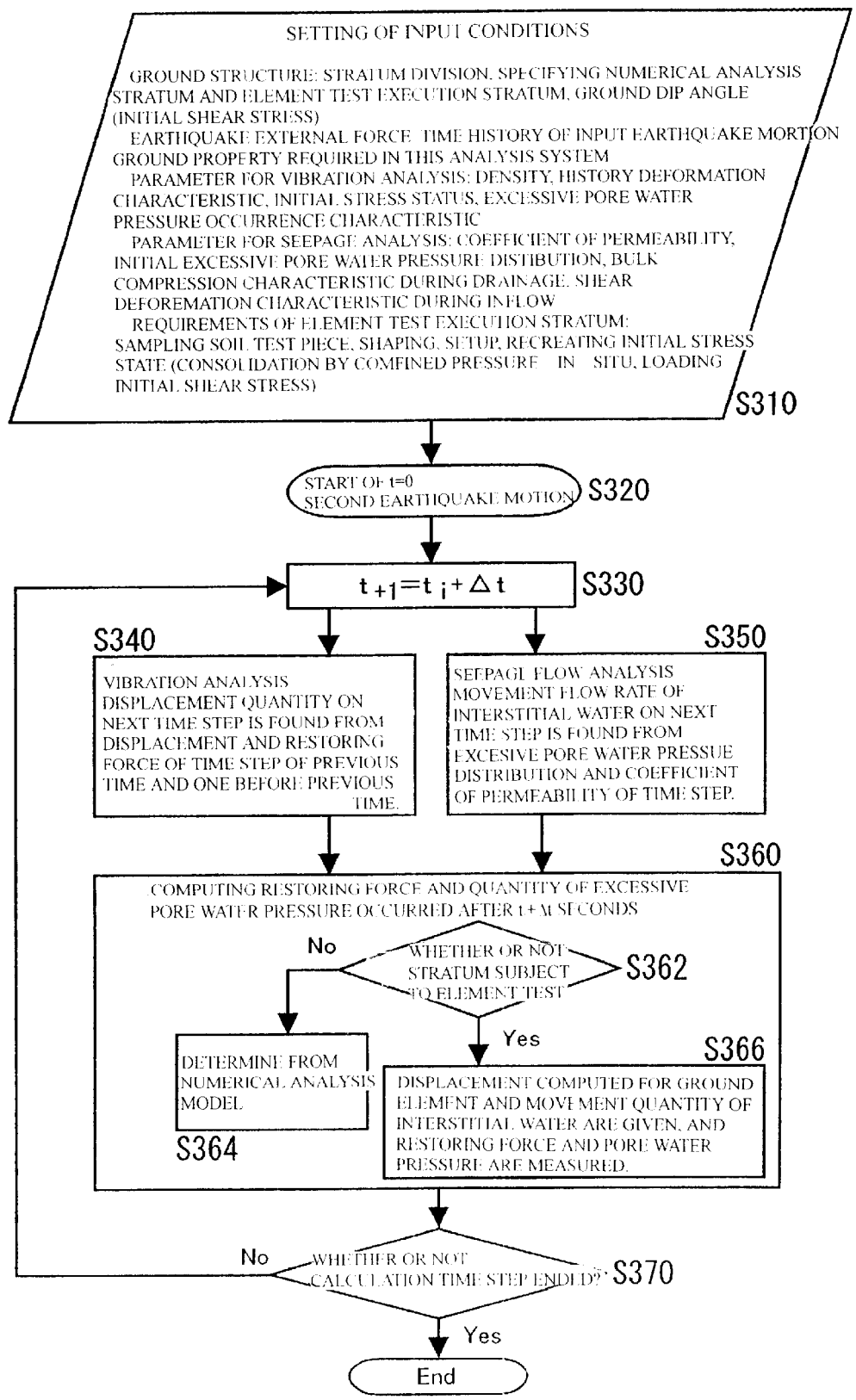

[Fig.07]
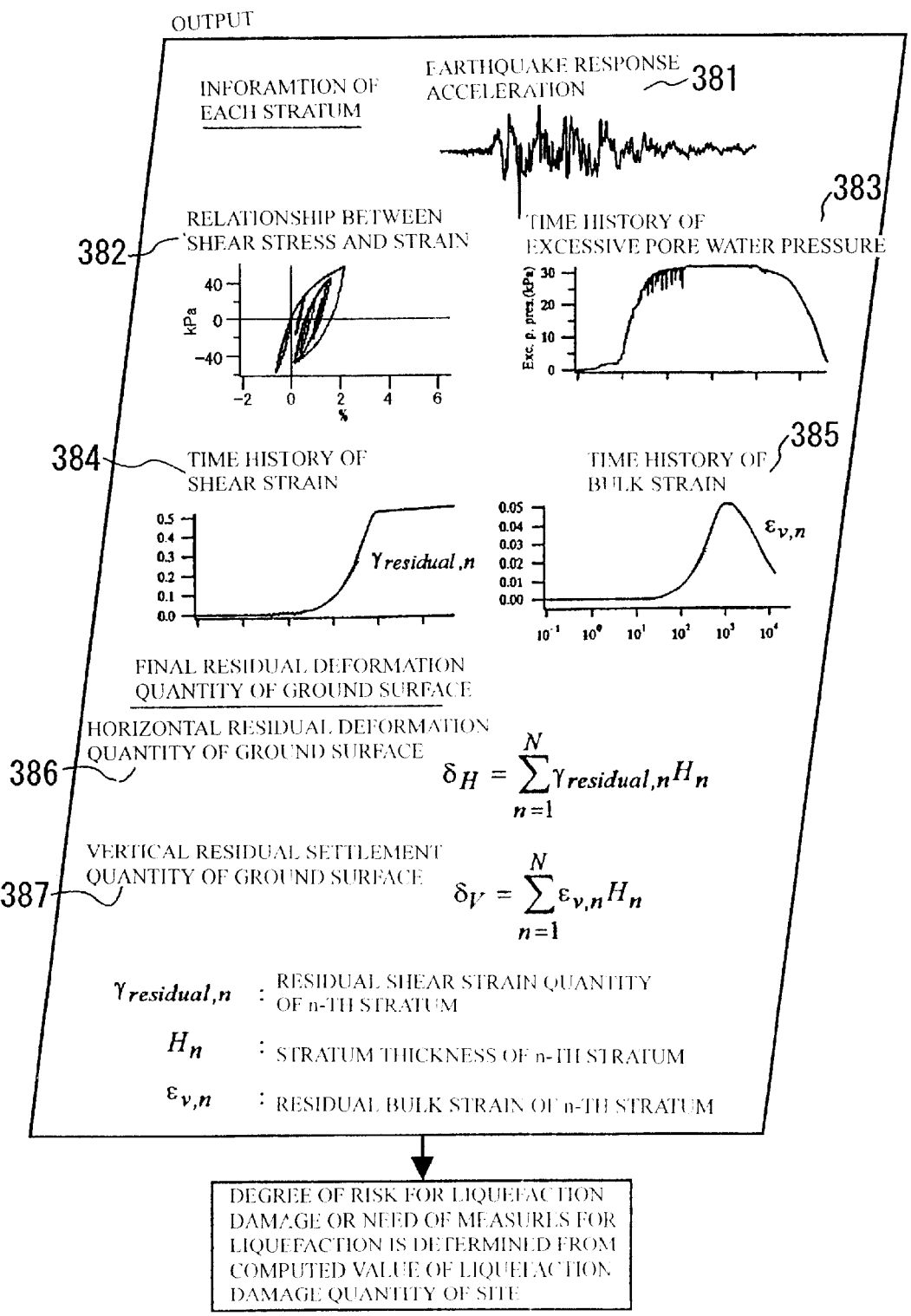

[Fig.08]
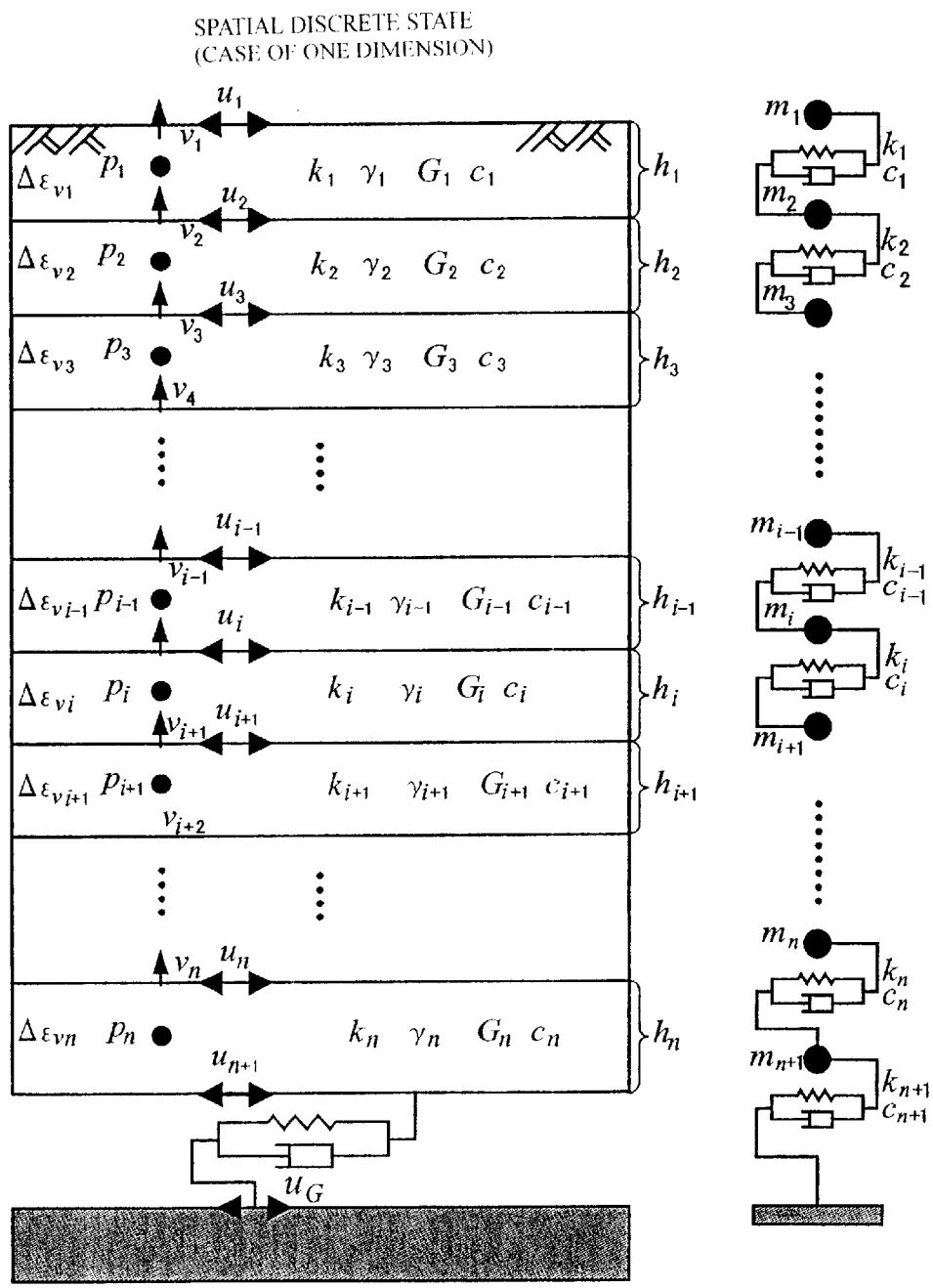
SPATIAL DISCRETE STATE
(CASE OF ONE DIMENSION)
$\gamma$   UNIT ARE WEIGHT     $u$   DISPLACEMENT
$G$   SHEAR RIGIDITY     $v$   SPEED OF INTERSTITIAL WATER
$m$   MASS     $\Delta\varepsilon_v$   BULK STRAIN INCREMENT
$k$   RIGIDITY     $p$   EXCESSIVE PORE WATER PRESSURE
$c$   VISCOSITY COEFFICIENT     $Q$   RESTORING FORCE

[Fig.09]
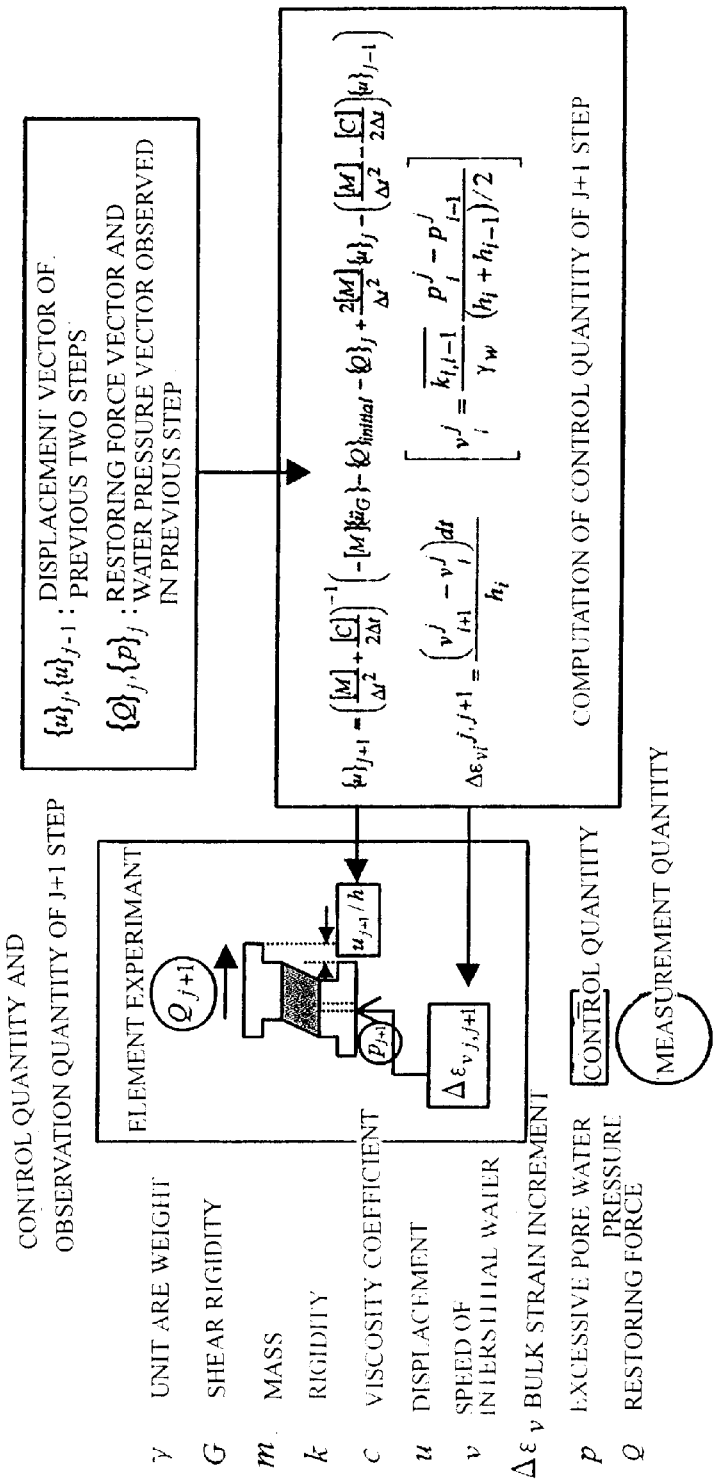

LIQUEFACTION PHENOMENON PREDICTION SYSTEM

BACKGROUND OF THE INVENTION

1. Field of the Invention

The present invention relates to a system to predict residual settlement quantity and residual horizontal deformation quantity of ground where a liquefaction phenomenon occurred due to earthquake.

2. Prior Art

Liquefaction of ground is a phenomenon where cyclic shear stress due to earthquake motion increases pore water pressure in saturated sandy ground and reduces shear rigidity of ground. It is the phenomenon where settlement of ground or buildings, floating of light-weight underground structure, damage of piles due to a lateral flow phenomenon, is occurred by reduction of ground rigidity. Because random settlement of buildings or enormous damage occurs to infrastructure facility commencing with lifeline if the liquefaction phenomenon occurs, risk of the liquefaction phenomenon occurrence is predicted before constructing facility, and measures are taken for liquefaction if necessary.

Conventionally, there has existed a method of predicting the liquefaction phenomenon, in which volume of shear stress that would occur during earthquake is computed (computing external force), undrained cyclic shear strength of ground is found (computing resistance force), the ratio of the both forces is found as a liquefaction safety factor $F_L$, and it is determined that the liquefaction phenomenon should occur when the value is 1 or less. However, this method is a bipolar prediction method predicting either the liquefaction phenomenon occurs or not, and is not a method that can explain a real phenomenon where damage quantity continuously and relatively differs depending on a magnitude relationship between the size of external force and the size of resistance. Particularly, a method capable of predicting an extent of damage by liquefaction is demanded regarding a structure requiring performance design.

It is possible to compute disaster quantity of soil structure or ground with occurrence of the liquefaction phenomenon during earthquake by the residual deformation quantity after the earthquake ends. Presently, as a method of predicting disaster deformation quantity, there exists a numerical analysis method where soil behavior is ideally modeled. The prediction accuracy of this method largely depends on modeling of the cyclic shear behavior of soil and on how the shear deformation behavior of soil in situ that would suffer earthquake can be truly modeled. However, universalization of the behavior of soil is not sufficient by the current technical level, and the complexity of the behavior of soil in situ has not been fully expressed.

Further, there has existed a problem that the conventional numerical analysis incorporated large uncertainty in modeling the cyclic shear behavior of soil. In particular, the behavior of soil after it suffered shear stress and its strain level became large is extremely important because it directly contributes to the residual deformation quantity of ground, but no ultimate solution exists in modeling this area.

In addition, the conventional numerical analysis method has paid attention solely to undrained shear behavior of soil, where it is assumed that interstitial water in soil does not move during vibration, and in most cases, only deformation during vibration is considered regarding the deformation. However, it has been made clear with eyewitness evidence of actual earthquake damage that the residual deformation quantity of ground during earthquake does not only occur during vibration but it also develops progressively after vibration, and therefore, a method of examining mechanism of deformation development after vibration and predicting deformation based on the mechanism is demanded.

FIG. 1 is an appearance where the liquefaction phenomenon occurs due to earthquake. When earthquake begins, in FIG. 1, excessive pore water pressure occurs due to cyclic shear. Although the excessive pore water pressure due to earthquake ceases after earthquake ends, deformation of ground caused by inflow and outflow of interstitial water occurs with the cease. The deformation of ground continues until the excessive pore water pressure resolves.

Accordingly, a possibility has been pointed out recently, that seepage of the excessive pore water pressure plays an important role in flow deformation mechanism after earthquake (Motoki Kazama et al., Flow deformation mechanism due to seepage failure after earthquake, The 36th Geotechnical Engineering Symposium, pp.2415–2416, 2001). Furthermore, it has been found out that a preliminary numerical analysis, where bulk compression characteristic when the excessive pore water pressure caused by the cyclic shear resolves (relationship between interstitial water drainage and recovery of effective stress) and shear deformation characteristic when interstitial water flows in (relationship between interstitial water inflow and shear strain) are assumed, can explain deformation quantity after earthquake naturally (Noriaki Sento et al., Prediction method of flow deformation due to seepage failure after earthquake, The 36th Geotechnical Engineering Symposium, pp.2417–2418, 2001).

Few studies have been made for deformation characteristic of soil at the point of the inflow and outflow of such interstitial water, and the inflow and outflow of interstitial water is determined by environmental boundary conditions, so that damage prediction has been limited only by a characteristic prehension test as an element.

SUMMARY OF THE INVENTION

The object of the present invention is to provide a system to accurately predict residual settlement quantity and residual horizontal deformation quantity of ground, where the liquefaction phenomenon occurred due to earthquake, after resolving excessive pore water pressure.

To achieve the above-described object, the present invention is a liquefaction phenomenon prediction system that comprises shear stress loading means that applies shear stress to a test piece from subject ground, interstitial water injecting means that gives interstitial water to the test piece, measuring means that measures displacement and a pore water pressure at certain time, and data collection/control means that collects data from the measuring means and controls the shear stress loading means and the interstitial water injecting means, in which the data collection/control means controls the shear stress loading means to apply earthquake motion to the test piece, performs vibration analysis and seepage flow analysis for the test piece every hour by data from the measuring means, controls the shear stress loading means and the interstitial water injecting means based on a result obtained, and thus finds final residual deformation quantity.

The vibration analysis and the seepage flow analysis in the data collection/control means can be performed by using the fact that, when the subject ground is spatially discretised into each stratum, each stratum satisfies a force balance equation regarding shear stress and a continuity equation of balance regarding the movement of interstitial water every hour.

The data collection/control means performs numerical analysis of a stratum where the characteristic of the subject ground is known, and a numerical analysis result can be used in the vibration analysis and seepage flow analysis for the stratum.

BRIEF DESCRIPTION OF THE DRAWINGS

FIG. 1 is a view explaining a phenomenon where liquefaction occurs due to earthquake.

FIG. 2 is a view showing a constitution of a basic experimental unit for executing the liquefaction phenomenon prediction system of the present invention.

FIG. 3 is a view showing a constitution of an experimental unit for executing the liquefaction phenomenon prediction system.

FIG. 4 is a view explaining an outline of the liquefaction prediction system.

FIG. 5 is a view explaining an analysis region is spatially discretised.

FIG. 6 is a view showing an analysis flow of the liquefaction phenomenon prediction system.

FIG. 7 is a view showing an analysis result output of the liquefaction phenomenon prediction system.

FIG. 8 is a detail view of spatial discrete state in the analysis region.

FIG. 9 is a view explaining algorithm of a specific sequential analysis of a liquefaction analysis in the spatial discrete state of FIG. 8.

PREFERRED EMBODIMENTS OF THE INVENTION

Preferred embodiments of the present invention will be described using the accompanying drawings.

The present invention is a system that replaces the cyclic shear behavior of soil not with a numerical model but with behavior that is directly obtained from element test for a soil sample in situ. In the present invention, this system can find the residual settlement quantity and the residual horizontal displacement of ground.

Furthermore, to predict the shear strain quantity that progressively develops after vibration, the present invention is a prediction system of seepage flow deformation quantity after earthquake, which has directly incorporated the behavior of soil element in situ as well as during earthquake using a seepage flow analysis that has incorporated mechanism where excessive pore water pressure occurred during earthquake penetrates and moves after vibration and ground thus fails and deforms.

FIG. 2 shows the entire experimental apparatus 100 used in the present invention.

In FIG. 2, a personal computer 160 performs from control of the experimental apparatus 100 to analog-to-digital conversion and data acquisition. The motor controller 158 receives a signal from the personal computer 160, and drives a shear stress control motor 128 that applies shear stress of earthquake to a test piece 110 and a interstitial water flow rate control motor 132 of an interstitial water flow rate control unit 130 that controls flow rate of the interstitial water. A laser displacement meter 136 measures penetration quantity of a piston 134 to give flow rate control feedback of interstitial water. A shear load meter 126 measures the shear stress working on the test piece 110. A non-contact type displacement meter 124 measures displacement at the head portion of the test piece 110 to find shear strain. A vertical load cell 122 measures vertical stress working on the test piece 110. A differential pressure gauge 138 measures the excessive pore water pressure in the test piece 110. A dynamic strain amplifier 154 converts a signal of a strain gauge type sensor (shear load cell 126 or vertical load cell 122) into a voltage signal. A pressure amplifier 156 converts a signal from the differential pressure gauge 138 or the laser displacement meter 136 into voltage. To perform analog-to-digital conversion to various kinds of measured signal voltage from each sensor or amplifier, it is concentrated on a BNC connector (central terminal) 150 of a preliminary step and then input to the personal computer 160.

When there are a plurality of test pieces 110 from the ground of experimental subject, a plurality of the shear stress control motors 128 that apply shear stress of earthquake, the interstitial water flow rate control units 130 that control flow rate of the interstitial water, or sensors in FIG. 2 are prepared as shown in FIG. 3, and thus experiment can be simultaneously performed to each test piece (211 to 221). There exists one BNC connector 150 and personal computer 160 in this case, as well.

Description will be made for the control of experiment performed using the experimental apparatus 200 and the relationship between a measurement value and the residual deformation quantity of ground using FIG. 4 to FIG. 7 with an example of slow sloping ground having a stratum structure as an object. FIG. 4, FIG. 5, FIG. 6 and FIG. 7 are a schematic view of this system, an assumed model, a processing flow for prediction, and an output from this system, respectively.

1) In FIG. 4, the test pieces are formed by sampling soil in situ (stratum B to D in FIG. 4) from the ground that could be greatly deformed by earthquake or seepage flow, and they are made to be stratums subject to element test. A stratum that is considered to have no possibility of liquefaction and a little deformation or a stratum whose characteristic is well-known may be substituted for a numerical model (stratum A in FIG. 4).

2) Next, to solve a vibration equation and the continuity equation of interstitial water with respect to a predetermined earthquake external force, a ground structure of a site to be analyzed is spatially discretised. Description will be made in FIG. 5. FIG. 5 is the view showing the appearance where stratums A to D are spatially discretised. In each stratum having density ρ and coefficient of permeability k, excessive interstitial water p, displacement u, and flow rate Q between the stratums are predicted and controlled. This is realized by the experimental apparatus 200 of FIG. 3. Thus, it is possible to directly reflect the cyclic shear characteristic of the actual soil in situ and the deformation characteristic during inflow and outflow of interstitial water with respect to a stratum subject to element test.

3) As described above, setting of input conditions in the flowchart of FIG. 6 is performed for the experimental apparatus of FIG. 3 (S310), and vertical stress, horizontal stress and initial shear stress, which are equivalent to applied load that the ground at a depth of the point suffers, are worked on to each test piece (soil collected in situ or virtual soil material). This recreates a stress status of soil before earthquake occurs. The number of the recreated status equal to the samples subject to element test is required.

The input conditions are:

Ground structure: Stratum division, Specifying numerical analysis stratum (stratum A) and element test execution stratum (stratum B to stratum D), Ground sloping angle (this determines the initial shear stress.)

Earthquake external force: Time history of input earthquake motion

Parameter for vibration analysis (this is used when earthquake motion works.): Density, History deformation characteristic, Initial stress status, Excessive pore water pressure occurrence characteristic Parameter for seepage analysis (this is used when earthquake motion works and when the excessive pore water pressure resolves after the earthquake.): Coefficient of permeability, Initial excessive pore water pressure distribution, Bulk compression characteristic during drainage, Shear deformation characteristic during inflow Others 4) Next, analysis is performed in every short time step when earthquake motion works and the excessive pore water pressure increases to cause a water pressure difference in a depth direction (S320 to S370), which is performed as follows.

① At certain time (at a certain time step), it is necessary that ground satisfy the force balance equation regarding shear stress and the continuity equation of balance regarding the movement of interstitial water. Details will be described later.

② In the control of experiment, the shear displacement and the movement quantity of interstitial water on the next time step are found using the shear stress measured on the previous time step and inertial force due to the pore water pressure and earthquake motion (vibration analysis: S340, seepage flow analysis: S350).

③ Next, the shear displacement and the movement quantity of interstitial water, which have been found, are given to the test piece, and the quantity of the shear stress and the pore water pressure, which has occurred as response, is obtained (S360). At this point, the stratum in the numerical analysis model is determined by a numerical analysis model (S364). In the element test execution stratum, displacement and the movement quantity of interstitial water, which have been computed into stratum element, are actually given to each element (test piece) in the experimental apparatus 200 to measure restoring force and the pore water pressure (S366).

④ By sequentially repeating the steps of ② and ③, the time step advances, and it is possible to simulate the behavior of a process while earthquake motion works and the excessive pore water pressure, which is residual at a point when earthquake motion ends, resolves.

5 Since the shear displacement quantity before/after earthquake is measured as the time history in the simulation process, the horizontal residual deformation quantity is directly found when the test ends (horizontal residual deformation quantity of ground surface in FIG. 7:386).

Further, since the bulk strain quantity before/after earthquake is measured as the time history in the simulation process in the same manner, the residual settlement quantity is directly found when the test ends (vertical residual settlement quantity of ground surface in FIG. 7:387).

Furthermore, when property of each ground element is given, a recurrence formula to be satisfied for each time step is obtained, and the time histories of the bulk strain (385) and the shear strain (384) of each ground element during earthquake and after earthquake are found by solving the formula for every time step sequentially.

As described, the value obtained after all phenomena end is the residual bulk strain and the residual shear strain of the stratum. The residual deformation quantity on the ground surface is expressed as sum of deformation quantity in each stratum. Accordingly, it is possible to determine a hazardous degree of liquefaction damage, the need of measures for liquefaction, or the like by a computed value of liquefaction damage quantity.

In advancing the procedure, one essential point of the present invention is a point where the history deformation characteristic of the ground, the excessive pore water pressure occurrence characteristic of the stratum where liquefaction could occur, the bulk compression characteristic when the excessive pore water pressure resolves, and the shear deformation characteristic during inflow of interstitial water are directly reflected by the element test of soil in situ.

Next, specific algorithm of sequential analysis will be described using FIG. 8 and FIG. 9. An equation of motion in a discrete multi-mass system, as shown in FIG. 8, can be generally expressed in equation (1).

[Equation 1]

$$[M]\{\ddot{u}\}+[C]\{\dot{u}\}+\{Q\}=[M]\{\ddot{u}_G\}-\{Q\}_{initial} \quad (1)$$

where [M]: Mass matrix having mass m as an element, [C]: Viscosity matrix having viscosity coefficient c as an element, {Q}: Restoring force vector having restoring force Q as an element, {u}: Displacement vector having relative displacement u from bedrock as an element, {$u_G$}: Displacement vector of bedrock, and {Q}$_{initial}$: Initial load vector (initial shear load vector).

On the other hand, continuity conditions of interstitial water Are expressed in the following equation (2).

[Equation 2]

$$\Delta \varepsilon_v = -\frac{k}{\gamma_w}\nabla^2 p \quad (2)$$

where $\Delta \epsilon_v$: Increment of bulk strain, k: Coefficient of permeability, $\gamma_w$: Specific weight of water, and p: Excessive pore water pressure.

When equation (2) is differentiated in spatial/time directions, seepage rate of interstitial water per unit area on a j step of an i stratum is expressed in the following equation (3).

[Equation 3]

$$v_i^j = \frac{\overline{k}_{i,i-1}}{\gamma_w}\frac{p_i^j - p_{i-1}^j}{(h_i + h_{i-1})/2} \quad (3)$$

where $p'_i$ and $p'_{i-1}$ are the excessive pore water pressure of the i–stratum and an i–1 stratum on the j step, and $h_i$ and $h_{i-1}$ are the stratum thickness of the i stratum and the i–1 stratum. Note that an average coefficient of permeability 'bar $k_{i,i-1}$' between the i stratum and an i–1 stratum is expressed in equation (4) using the coefficient of permeability $k_{i-1}$ and $k_i$ of each stratum.

[Equation 4]

$$\overline{k}_{i,i-1} = \frac{h_{i-1}+h_i}{h_{i-1}/k_{i-1}+h_i/k_i} \quad (4)$$

Finally, a bulk strain increment $\Delta \epsilon_{vi}^{j,j+1}$ from the j step to an j+1 step of the i stratum is expressed in equation (5).

[Equation 5]

$$\Delta \varepsilon_{vi}^{j,j-1} = \frac{(v_{i+1}^j - v_i^j)\Delta t}{h_i} \quad (5)$$

On the other hand, when equation (1) is differentiated in a time direction and the relative displacement $\{u\}_{j+1}$ of the j+1 step is expressed using the relative displacement $\{u\}_j$ and $\{u\}_{j-1}$ of the j step and a j−1 step, equation (6) is obtained.

[Equation 6]

$$\{u\}_{j+1} = \left(\frac{[M]}{\Delta t^2} + \frac{[C]}{2\Delta t}\right)^{-1} \left(-[M]\{ii_G\} - \{Q\}_{initial} - \{Q\}_j + \frac{2[M]}{\Delta t^2}\{u\}_j - \left(\frac{[M]}{\Delta t^2} - \frac{[C]}{2\Delta t}\right)\{u\}_{j-1}\right) \quad (6)$$

where $\{Q\}_j$ is the restoring force vector obtained by the element experiment where $\{u\}_j$ and $\{\Delta\epsilon_v\}_{j-1,j}$ are given as a control value.

The foregoing is summarized as follows as shown in FIG. 9.

① $\{u\}_{j+1}$ is found by $\{u\}_j$, $\{u\}_{j-1}$ (analysis values on previous two steps) and $\{Q\}_j$ (restoring force vector observed in a previous step) (refer to Equation (6)). $\{\Delta\epsilon_v\}_{j, j+1}$ is found by $\{p\}_j$ (water pressure vector observed in the previous step) (refer to Equation (3) to Equation (6)).

② $\{u\}_{j+1}$ and $\{\Delta\epsilon_v\}_{j, j+1}$ are given as the control value by the element experiment, and thus finding $\{Q\}_{j+1}$ and $\{p\}_{j+1}$.

Initial conditions corresponding to a problem are given, the above-described operations of ① and ② are sequentially repeated, and thus finding the residual deformation quantity of ground for a predetermined earthquake external force.

The above-described experimental control algorithm is another essential point of the present invention.

Note that the above-described system can be applied not only for the analysis of residual deformation during earthquake but for a so-called consolidation settlement analysis (when earthfill is made or load of a structure works on clay ground of poor permeability, interstitial water in the clay is gradually squeezed out, which results in a phenomenon that causes ground settlement for a long period of time).

As described above, with the use of the constitution of the present invention, it is possible to accurately predict the residual settlement quantity and residual horizontal deformation quantity after the excessive pore water pressure in the ground, where liquefaction has occurred due to earthquake, resolves.

What is claimed is:

1. A liquefaction phenomenon prediction system, comprising:

shear stress loading means that applies shear stress to a test piece from subject ground;

interstitial water injecting means that gives interstitial water to said test piece;

measuring means that measures displacement and a pore water pressure at certain time; and data collection/control means that collects data from said measuring means and controls said shear stress loading means and said interstitial water injecting means, wherein said data collection/control means controls the shear stress loading means to apply earthquake motion to said test piece, performs vibration analysis and seepage flow analysis for said test piece every hour by data from the measuring means, controls said shear stress loading means and said interstitial water injecting means based on a result obtained, and thus finds final residual deformation quantity.

2. The liquefaction phenomenon prediction system according to claim 1, wherein the vibration analysis and the seepage flow analysis in said data collection/control means are performed by using the fact that, when subject ground is spatially discretised into each stratum, each stratum satisfies a force balance equation regarding shear stress and a continuity equation of balance regarding movement of interstitial water.

3. The liquefaction phenomenon prediction system according to claim 2 wherein said data collection/control means performs numerical analysis of a stratum of the subject ground, whose characteristic is known, and a numerical analysis result is used in the vibration analysis and seepage flow analysis for the stratum.

4. The liquefaction phenomenon prediction system according to claim 1, wherein said data collection/control means performs numerical analysis of a stratum of the subject ground, whose characteristic is known, and a numerical analysis result is used in the vibration analysis and seepage flow analysis for the stratum.

* * * * *